(12) United States Patent
Maekawa

(10) Patent No.: US 12,004,714 B2
(45) Date of Patent: Jun. 11, 2024

(54) MEDICAL INSTRUMENT

(71) Applicant: OLYMPUS CORPORATION, Tokyo (JP)

(72) Inventor: Yuto Maekawa, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 779 days.

(21) Appl. No.: 17/184,919

(22) Filed: Feb. 25, 2021

(65) Prior Publication Data

US 2021/0196303 A1 Jul. 1, 2021

Related U.S. Application Data

(63) Continuation of application No. PCT/JP2018/031933, filed on Aug. 29, 2018.

(51) Int. Cl.
*A61B 1/015* (2006.01)
*A61B 1/00* (2006.01)
(Continued)

(52) U.S. Cl.
CPC .......... *A61B 1/00147* (2013.01); *A61B 1/015* (2013.01); *A61B 1/018* (2013.01);
(Continued)

(58) Field of Classification Search
CPC . A61B 1/00135; A61B 1/00147; A61B 1/015; A61B 1/018; A61B 17/068;
(Continued)

(56) References Cited

U.S. PATENT DOCUMENTS 5,685,147 A * 11/1997 Brassea .................. F03B 17/02
60/495
2014/0120496 A1 5/2014 Rothenwaender et al.
(Continued)

FOREIGN PATENT DOCUMENTS

EP 1 210 974 A2 6/2002
JP 2002-326022 A 11/2002
(Continued)

OTHER PUBLICATIONS

International Search Report dated Nov. 13, 2018 received in PCT/JP2018/031933.

*Primary Examiner* — George Manuel
(74) *Attorney, Agent, or Firm* — Scully, Scott, Murphy & Presser, P.C.

(57) ABSTRACT

A medical instrument includes an insertion section main body extending along a longitudinal axis, a rotation supporter attached to the insertion section main body, a power transmission member rotatably supported by the rotation supporter and having a blade to which a fluid is supplied, external teeth arranged on an outer circumferential surface of the power transmission member in a circumferential direction, a tubular rotation member disposed outside the power transmission member in a radial direction, internal teeth arranged on an inner circumferential surface of the rotation member in the circumferential direction, and a fluid duct configured to supply the fluid to the blade. The power transmission member is configured to rotate by receiving power generated in the blade due to supply of the fluid. The rotation member is configured to rotate about the longitudinal axis by receiving the power from the power transmission member as the internal teeth are meshed with the external teeth.

20 Claims, 12 Drawing Sheets

(51) Int. Cl.
    *A61B 1/018*     (2006.01)
    *A61B 17/32*     (2006.01)
    *F01D 15/06*     (2006.01)
    *A61B 17/00*     (2006.01)

(52) U.S. Cl.
    CPC ........ *A61B 17/32002* (2013.01); *F01D 15/06* (2013.01); *A61B 2017/00022* (2013.01); *A61B 2017/00415* (2013.01)

(58) Field of Classification Search
    CPC .............. A61B 17/29; A61B 17/32002; A61B 2017/00022; A61B 2017/00296; A61B 2017/0034; A61B 2017/00415; A61B 2017/00539; A61B 2017/2929; A61B 2017/2937; F01D 15/06
    See application file for complete search history.

(56) References Cited

U.S. PATENT DOCUMENTS

2015/0216551 A1\*   8/2015   Dieras ............ A61B 17/320068
                                                             606/169
2018/0238883 A1\*   8/2018   Penny ....................... B25J 9/14

FOREIGN PATENT DOCUMENTS

| | | |
|---|---|---|
| JP | 2004-512892 A | 4/2004 |
| JP | 4091424 B2 | 5/2008 |
| JP | 2009-077844 A | 4/2009 |
| JP | 2010-227159 A | 10/2010 |
| JP | 2014-083447 A | 5/2014 |
| JP | 2016-152917 A | 8/2016 |
| WO | 02/38037 A2 | 5/2002 |

\* cited by examiner

MEDICAL INSTRUMENT

The present disclosure relates to a medical instrument including a rotation mechanism. This application is a continuation application based on PCT Patent Application No. PCT/JP2018/031933, filed Aug. 29, 2018, the content of which is incorporated herein by reference.

BACKGROUND

A medical instrument such as an endoscopic device, a surgical stapler, or the like, including a rotation mechanism in an insertion section inserted into a lumen is known. In such a medical instrument, a wire or a cable is used as a transmission member configured to transmit a rotational torque for rotating the rotation mechanism provided on a distal end of an elongated insertion section.

A cutting device inserted and used in a lumen is disclosed in Published Japanese Translation No. 2004-512892 of the PCT International Publication. The cutting device includes a staple mechanism configured to push a plurality of staples and provided at a distal portion thereof. An operator of the cutting device rotates an operating handle provided on a proximal end of the device, thereby a driving cable is rotated, and a cam mechanism provided in the staple mechanism is rotated. The staple mechanism sequentially pushes a plurality of staples by rotating the cam mechanism about a longitudinal axis.

SUMMARY

A medical instrument according to a first aspect of the present disclosure includes: an insertion section main body extending along a longitudinal axis; a rotation supporter attached to the insertion section main body; a power transmission member configured to be rotatably supported by the rotation supporter, and having a blade to which a fluid is supplied; external teeth arranged on an outer circumferential surface of the power transmission member in a circumferential direction; a rotation member having a tubular shape and disposed outside the power transmission member in a radial direction; internal teeth arranged on an inner circumferential surface of the rotation member in the circumferential direction; and a fluid duct configured to supply the fluid to the blade. The power transmission member is configured to rotate by receiving power generated in the blade due to supply of the fluid, and the rotation member is configured to rotate about the longitudinal axis by receiving the power from the power transmission member as the internal teeth are meshed with the external teeth.

In the medical instrument according to the first aspect, the power transmission member may be a tubular member, and the power transmission member may be fitted onto an outer circumferential surface of the rotation supporter.

In the medical instrument according to the second aspect, the external teeth may be arranged at equal intervals on the outer circumferential surface in the circumferential direction.

In the medical instrument according to any one of the first to third aspects, the power transmission member may be a tubular member, and a plurality of the blade may be arranged on the inner circumferential surface of the power transmission member in the circumferential direction.

In the medical instrument according to any one of the first to third aspects, the power transmission member may be a tubular member, and a plurality of blade may be arranged on the outer circumferential surface of the power transmission member in the circumferential direction.

The medical instrument according to the fifth aspect may further include a casing member that forms an annular flow path including the blades on the outer circumferential surface of the power transmission member so as to include the blades, wherein the fluid duct may be configured to communicate with the annular flow path.

The medical instrument according to the sixth aspect further includes a seal member having a ring-shape, and configured to prevent a fluid from flowing out from the annular flow path.

The medical instrument according to any one of the first to seventh aspects may further include a sensor configured to detect rotation of the rotation member; and a controller configured to control at least one of a pressure of the fluid, a flow rate and a direction of the fluid on the basis of rotation number information obtained from the sensor.

A medical instrument according to the ninth aspect includes: an insertion section main body extending along a longitudinal axis; a power transmission member having a tubular shape and supported by the insertion section main body so as to be rotatable with respect to the insertion section main body; a rotation member disposed outside from an inner surface of the power transmission member in a radial direction; and a fluid duct configured to supply the fluid to the power transmission member, wherein the power transmission member is configured to rotate by receiving power generated due to supply of the fluid, and the rotation member is configured to rotate about the longitudinal axis in accordance with a rotation of the power transmission member.

In the medical instrument according to the ninth aspect, the power transmission member may a blade to which a fluid is supplied, and the power transmission member may be configured to rotate by receiving power generated in the blade due to supply of the fluid.

In the medical instrument according to the tenth aspect, the blade may be a flat plate-shaped member elongated from an outer circumferential surface of the power transmission member in a normal direction of the outer circumferential surface.

In the medical instrument according to the tenth aspect, the blade may have a curved surface.

In the medical instrument according to the tenth aspect, a plurality of the blade may be arranged on an inner circumferential surface of the power transmission member in a circumferential direction.

In the medical instrument according to the tenth aspect, a plurality of blade may be arranged on an outer circumferential surface of the power transmission member in a circumferential direction.

The medical instrument according to the fourteenth aspect may include a casing member that forms an annular flow path on an outer circumferential surface of the power transmission member so as to include the blades. The fluid duct may be configured to communicate with the annular flow path.

The medical instrument according to the ninth aspect may include: a sensor configured to detect rotation of the rotation member; and a controller configured to control at least one of a pressure of the fluid, a flow rate and a direction of the fluid on the basis of rotation number information obtained from the sensor.

The medical instrument according to the ninth aspect may include a rotation supporter attached to the insertion section main body, and has a rigidity greater than a rigidity of the insertion section main body. The power transmission member may be rotatably fitted onto an outer circumference surface of the rotation supporter.

In the medical instrument according to ninth aspect, the rotation member may be disposed outside the power transmission member in a radial direction.

The medical instrument according to the ninth aspect may include external teeth arranged on an outer circumferential surface of the power transmission member in a circumferential direction; and internal teeth arranged on an inner circumferential surface of the rotation member in the circumferential direction. The rotation member may be configured to rotate about the longitudinal axis by receiving the power from the power transmission member as the internal teeth are meshed with the external teeth.

In the medical instrument according to the nineteenth aspect, the external teeth may be arranged at equal intervals on the outer circumferential surface in the circumferential direction.

DETAILED DESCRIPTION OF THE PREFERRED EMBODIMENTS

First Embodiment

Figure 1:
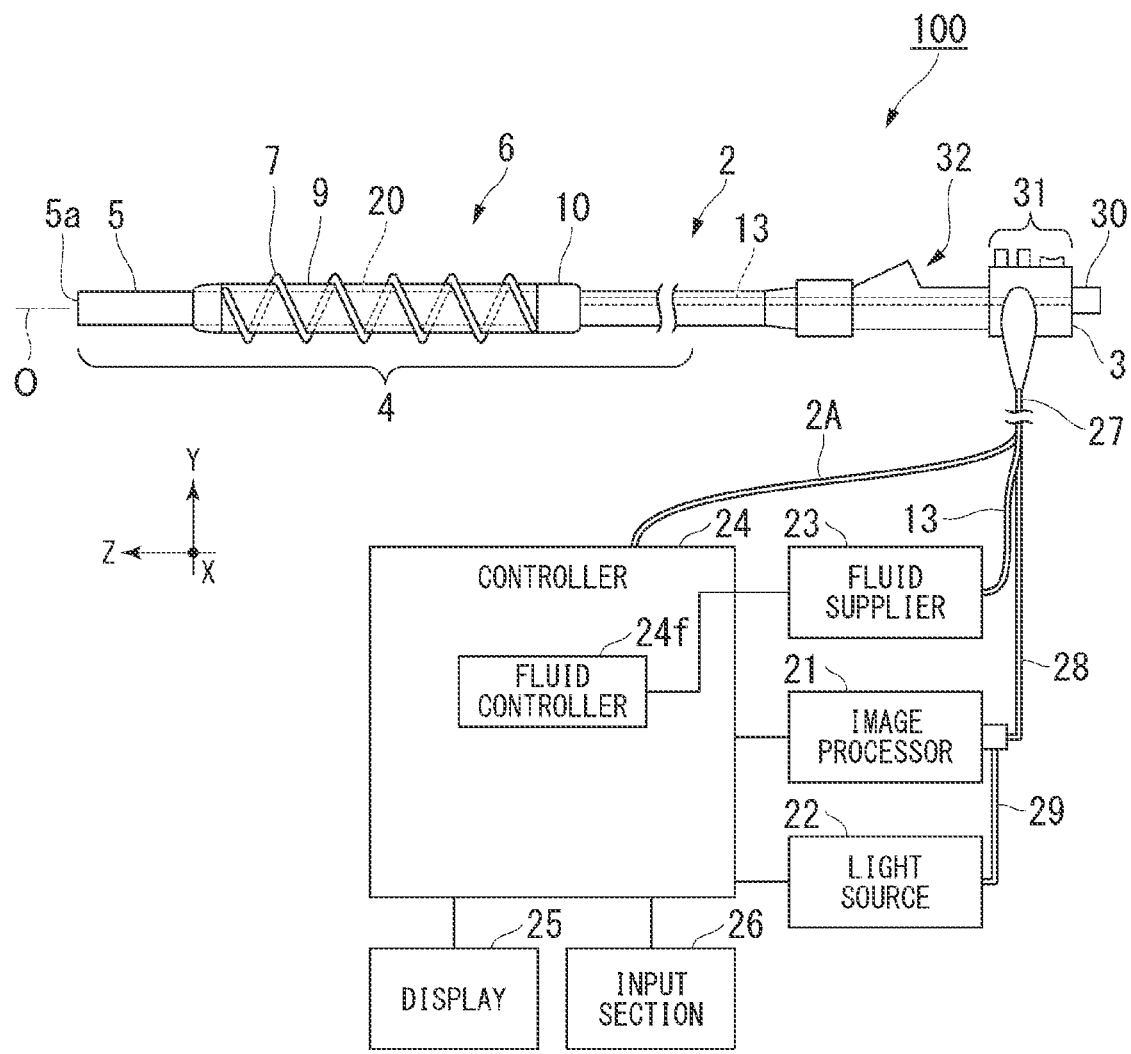
FIG. 1 is a view showing a conceptual appearance configuration of an endoscopic device that is a medical instrument according to a first embodiment.

A first embodiment will be described with reference to FIGS. 1 to 8.
[Endoscopic Device (Medical Instrument) 100]
FIG. 1 is a conceptual appearance configuration of an endoscopic device 100 that is a medical instrument according to the embodiment. As shown in FIG. 1, the endoscopic device (the medical instrument) 100 includes an insertion section 2 inserted into a lumen of a living body, an operating unit 3 provided on the side of a proximal end of the insertion section 2, and a driving system 20.

As shown in FIG. 1, the insertion section 2 includes: an elongated insertion section main body 4; a curved section 5; a living body insertion mechanism 6; and a rotation mechanism 10. The insertion section main body 4 extends along a longitudinal axis O of the insertion section 2. The curved section 5 is provided on a distal side of the insertion section main body 4. An axial center of the insertion section 2 is coaxial with the longitudinal axis O. The insertion section 2 is configured to be inserted into a body cavity upon use of the endoscopic device 100.

The curved section 5 is an elongated member curved to match the curve of the lumen. An imaging section (not shown) is provided on a distal portion 5a of the curved section 5.

The living body insertion mechanism 6 is a tubular member. The living body insertion mechanism 6 is fitted onto the insertion section main body 4 or an outer circumference of the curved section 5 with a gap therebetween, and is detachably attached to the rotation mechanism 10. The living body insertion mechanism 6 has a fin 7 and a spiral tube (an introduction propulsion part) 9. The fin 7 functions as a propulsion area and a retracting area. The spiral tube (an introduction propulsion part) 9 rotates about a longitudinal axis and functions for introduction propulsion.

The fin 7 is spirally wound on an outer circumference of the spiral tube 9. The living body insertion mechanism 6 advances in the lumen by rotating the spiral tube 9 in a direction opposite to a spiral direction in which the fin 7 is wound. On the other hand, the living body insertion mechanism 6 retracts in the hollow organ by rotating the spiral tube 9 in the spiral direction in which the fin 7 is wound.

The spiral tube 9 have a material (for example, a rubber material or a resin material), a structure, or the like, such that the spiral tube 9 has flexibility so as to curve along a curve of the curved section 5. A distal part of the spiral tube 9 is formed in a distal-tapered shape thereby the spiral tube 9 is capable of being easily inserted into the hollow organ.

The living body insertion mechanism 6 is a throwaway article (a disposable article). The living body insertion mechanism 6 is detachably attached to the rotation mechanism 10 and is capable of being exchanged after every treatment for prevention of infection.

The rotation mechanism 10 rotates the spiral tube 9 about the longitudinal axis of the insertion section 2 to assist introduction of the insertion section 2 into the hollow organ. The rotation mechanism 10 is capable of rotating the spiral tube 9 in both directions (CW, CCW).

A fluid duct 13 passes through the insertion section 2. The fluid duct 13 is connected to the rotation mechanism 10. The fluid duct 13 is connected to a fluid supply supplier 23, which will be described below. A part of the rotation mechanism 10 is rotated by a fluid supplied from the fluid supply supplier 23.

An operating knob 30 and a switch 31 are disposed in the operating unit 3. The operating knob 30 and the switch 31 are configured to perform various operations including a bending operation of the curved section 5 or rotation of the rotation mechanism 10. A treatment tool insertion section 32 into which a treatment tool is inserted is provided on the operating unit 3.
[Driving System 20]

The driving system 20 has an image processor 21 configured to process an image captured by an imaging section, a light source 22 configured to emit illumination light that illuminates an imaging target, a fluid supplier 23, a controller 24 configured to control whole of device including each of performing sections, a display 25 configured to display the captured image or the like, and an input section 26 configured to input an instruction or the like to the controller 24.

The image processor 21 processes the image captured by the imaging section. The image processor 21 may be an electronic circuit dedicated to image processing, or may be a program-executable computer included by a processor, a memory, and the like. The image processor 21 is connected to the imaging section by an imaging cable 28 that transmits an imaging signal.

The light source 22 emits illumination light that illuminates an imaging target. The light source 22 is connected to a light guide 29 configured to guide illumination light. The light emitted from the light source 22 is guided by the light guide 29, and radiated to the imaging target from the distal portion 5a of the curved section 5.

A fluid for rotating a part of the rotation mechanism 10 is stored in the fluid supplier 23. The fluid is supplied to the rotation mechanism 10 via the fluid duct 13 connected to the fluid supplier 23. The fluid is water that is usable in a living body for cleaning or the like. The fluid supplied to the rotation mechanism 10 is delivered to the fluid supplier 23 via the fluid duct 13. Supply of the fluid from the fluid supplier 23 to the rotation mechanism 10 is performed on the basis of an instruction of the controller 24.

The controller 24 has a fluid controller 24f configured to control the fluid in the fluid supplier 23. The controller 24 may be an electronic circuit dedicated to control, or may be a program-executable computer constituted by a processor, a memory, or the like.

The display 25 is constituted by, for example, a liquid crystal monitor. The display 25 is configured to display the captured image. The display 25 is also capable of displaying the information (for example, position information or the like) related to the captured image in the same screen.

A universal cable 27 is a cable that integrates the imaging cable 28, the light guide 29, the fluid duct 13, and a control cable 2A connected to the controller 24. The universal cable 27 is connected to the operating unit 3 by a connector.

[Rotation Mechanism 10]

Figure 2:
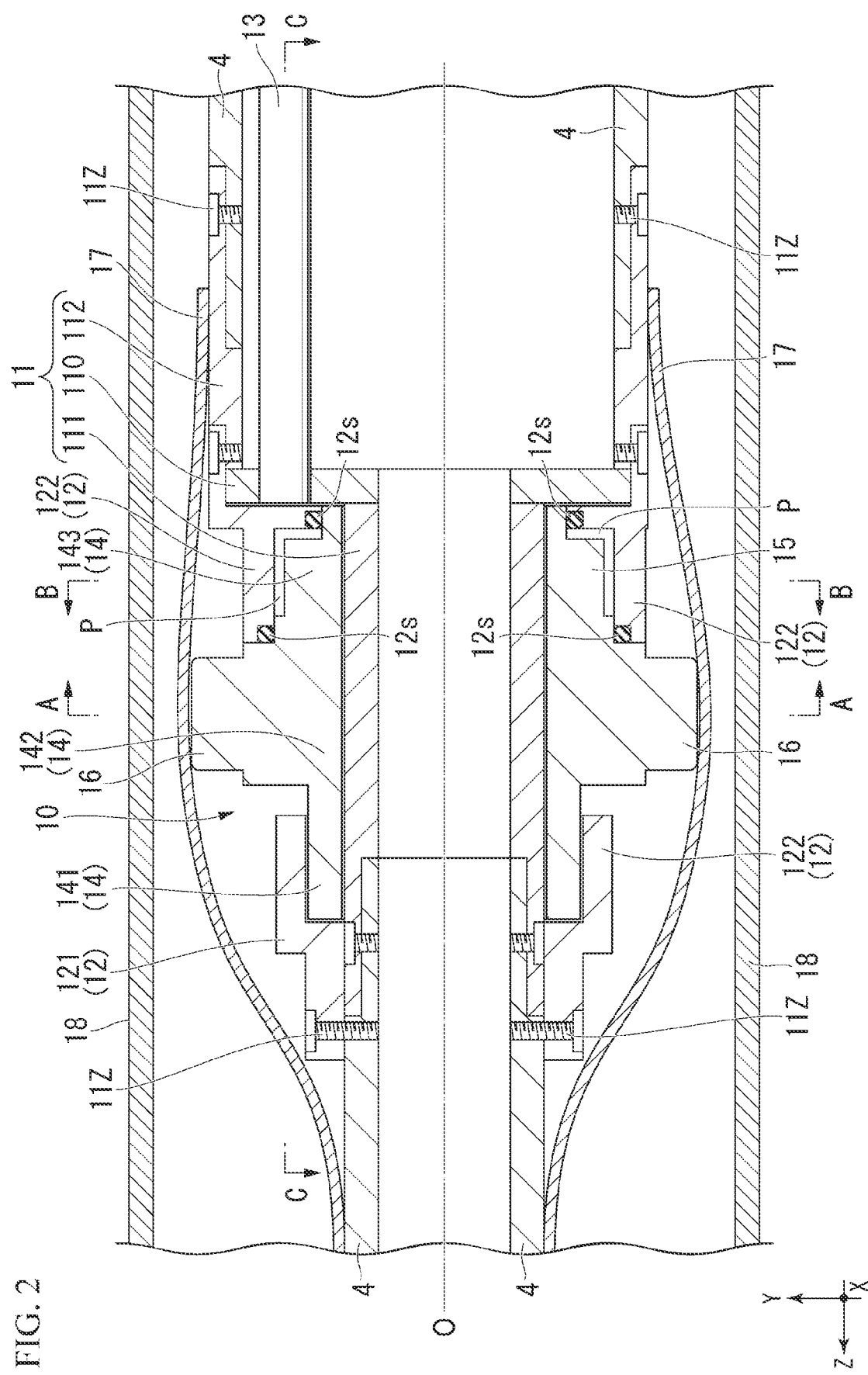
FIG. 2 is a cross-sectional view of an insertion section of the endoscopic device in a longitudinal axis direction.
Figure 3:
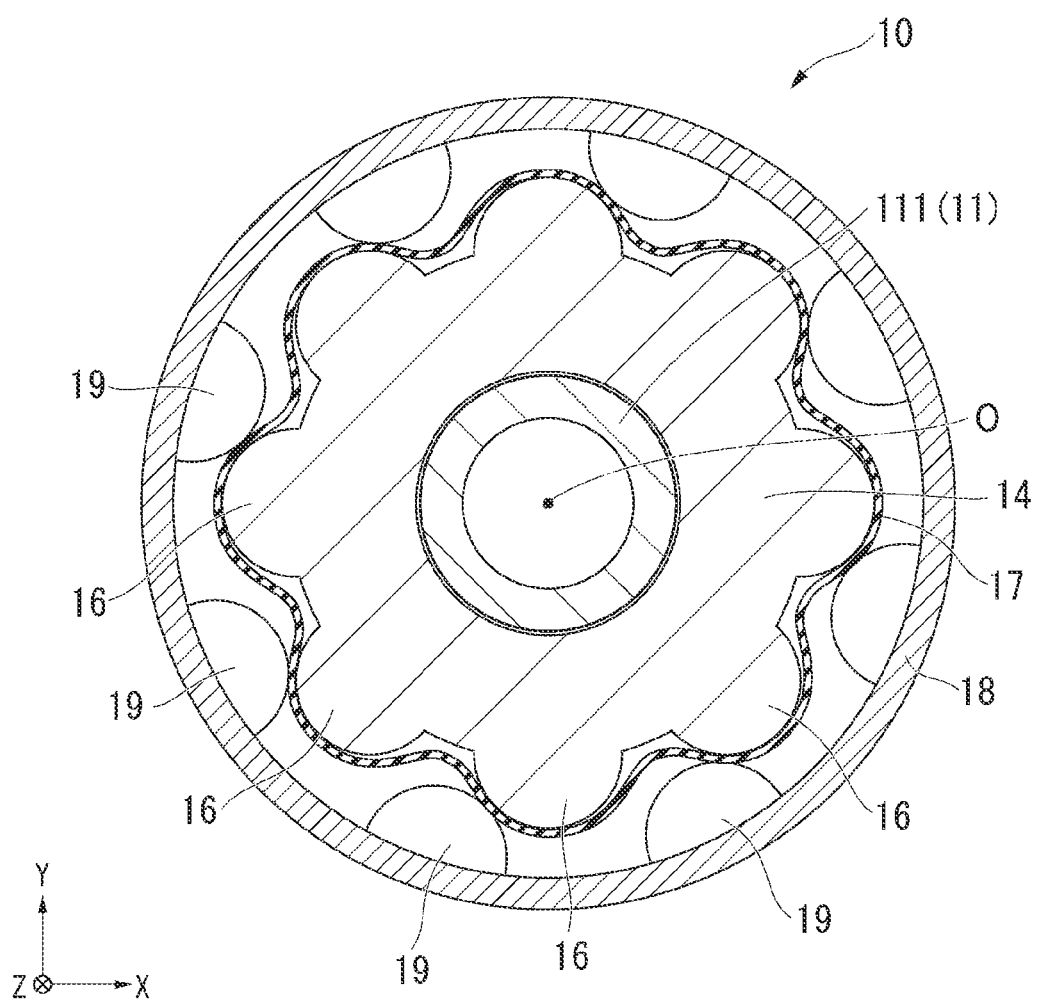
FIG. 3 is a cross-sectional view taken along a cross section A-A perpendicular to a longitudinal axis of the insertion section shown in FIG. 2.
Figure 4:
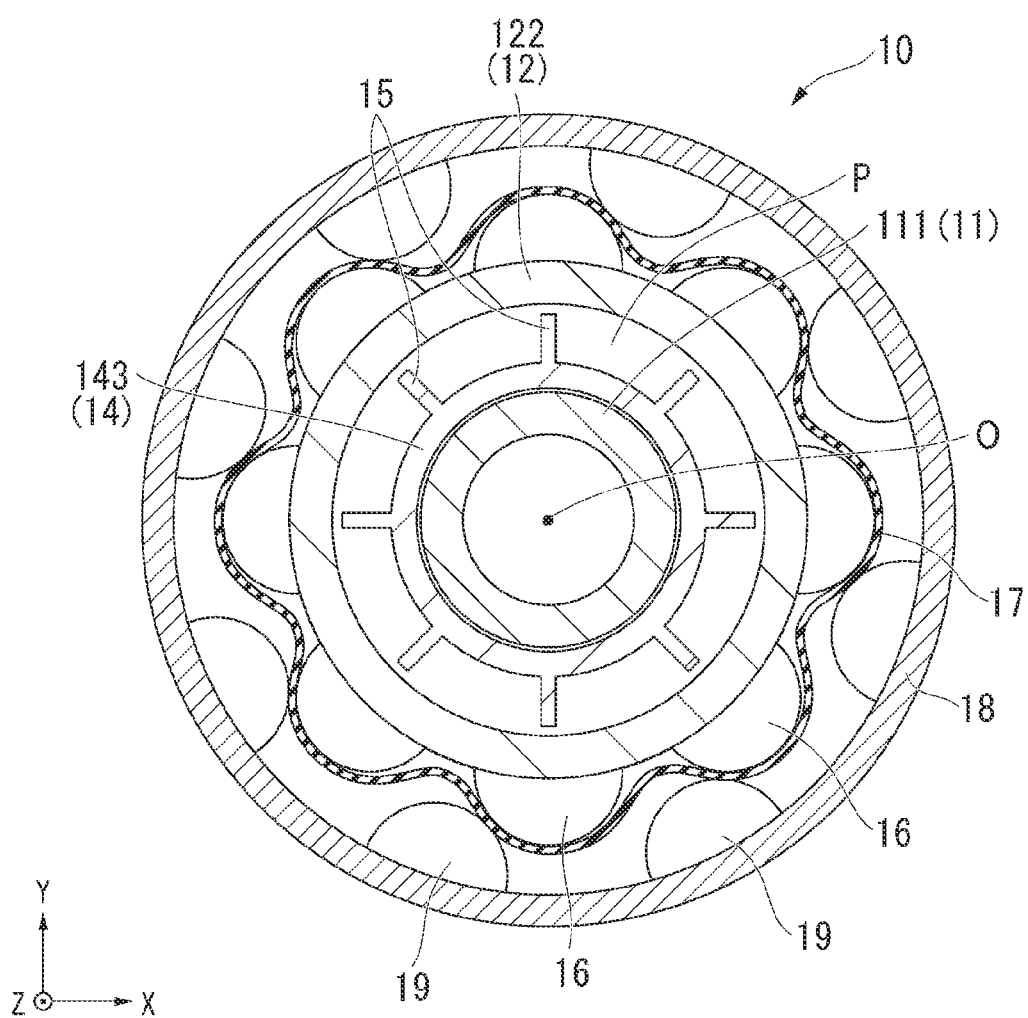
FIG. 4 is a cross-sectional view taken along a cross section B-B perpendicular to the longitudinal axis of the insertion section shown in FIG. 2.

FIG. 2 is a cross-sectional view of the insertion section 2 in a longitudinal axis O direction. FIG. 3 is a cross-sectional view taken along a cross section A-A perpendicular to the longitudinal axis O of the insertion section 2 shown in FIG. 2. FIG. 4 is a cross-sectional view taken along a cross section B-B perpendicular to the longitudinal axis O of the insertion section 2 shown in FIG. 2. In the following description, the cross section A-A and the cross section B-B are also referred to as an XY plane, and the longitudinal axis O direction of the insertion section 2 is also referred to as a Z-axis direction.

As shown in FIG. 2, the rotation mechanism 10 has a rotation supporter 11, a casing 12, an inner rotation tube (a power transmission member) 14, a covering member 17, and an outer rotation tube (a rotation member) 18. The covering member 17 is configured to cover the inner rotation tube 14.

The rotation supporter 11 is a cylindrical member provided on an intermediate section of the insertion section main body 4 that is flexible. The rotation supporter 11 has a rigidity greater than that of the insertion section main body 4. The rotation supporter 11 rotatably supports the inner rotation tube 14 fitted onto the outer circumferential part of the rotation supporter 11. The rotation supporter 11 is connected to the insertion section main body 4 by screws 11z at a distal part and a proximal part such that watertightness is maintained.

The rotation supporter 11 has a first rotation supporter 111, a second rotation supporter 112, and a connecting part 110. Both of the first rotation supporter 111 and the second rotation supporter 112 are cylindrical members. A dimension of the first rotation supporter 111 in the radial direction is smaller than a dimension of the second rotation supporter 112 in the radial direction. The first rotation supporter 111 and the second rotation supporter 112 are disposed from the distal side toward the proximal side, and the proximal end of the first rotation supporter 111 and the distal end of the second rotation supporter 112 are connected via the connecting part 110.

The connecting part 110 is a ring-shaped member. The connecting part 110 connects the proximal end of the first rotation supporter 111 and the distal end of the second rotation supporter 112 with no gap except two through-holes (a first through-hole 11a and a second through-hole 11b), which will be described below. An internal space of the first rotation supporter 111 communicates with an internal space of the second rotation supporter 112 without being interrupted by the connecting part 110.

As shown in FIG. 2, the casing 12 is a member configured to limit retracting movement of the inner rotation tube 14 in a longitudinal direction. The casing 12 has a first casing 121 and a second casing 122.

The first casing 121 is a ring-shaped member. The first casing 121 is fitted onto an outer circumference of the first rotation supporter 111. The distal end of the first casing 121 is relatively immovably attached to the first rotation supporter 111 on the distal side than the inner rotation tube 14.

The second casing 122 is a ring-shaped member, and is fitted onto outer circumferences of the first rotation supporter 111 and the second rotation supporter 112. The proximal end of the second casing 122 is relatively immovably attached to the second rotation supporter 112 on more proximal side than the inner rotation tube 14.

As shown in FIG. 3, the inner rotation tube (the power transmission member) 14 is a cylindrical member fitted with the first rotation supporter 111 with a gap with respect to an outer circumference of the first rotation supporter 111. The inner rotation tube 14 is supported by the first rotation supporter 111 so as to rotate about the longitudinal axis O. As shown in FIG. 3, the inner rotation tube 14 has a plurality of external teeth 16 arranged at equal intervals on an outer circumferential surface in a circumferential direction.

While the inner rotation tube 14 is rotatable about the longitudinal axis O, since the inner rotation tube 14 is sandwiched by the first casing 121 and the second casing 122, the inner rotation tube 14 is not capable of forwarding and retracting in the longitudinal axis direction.

Figure 5:
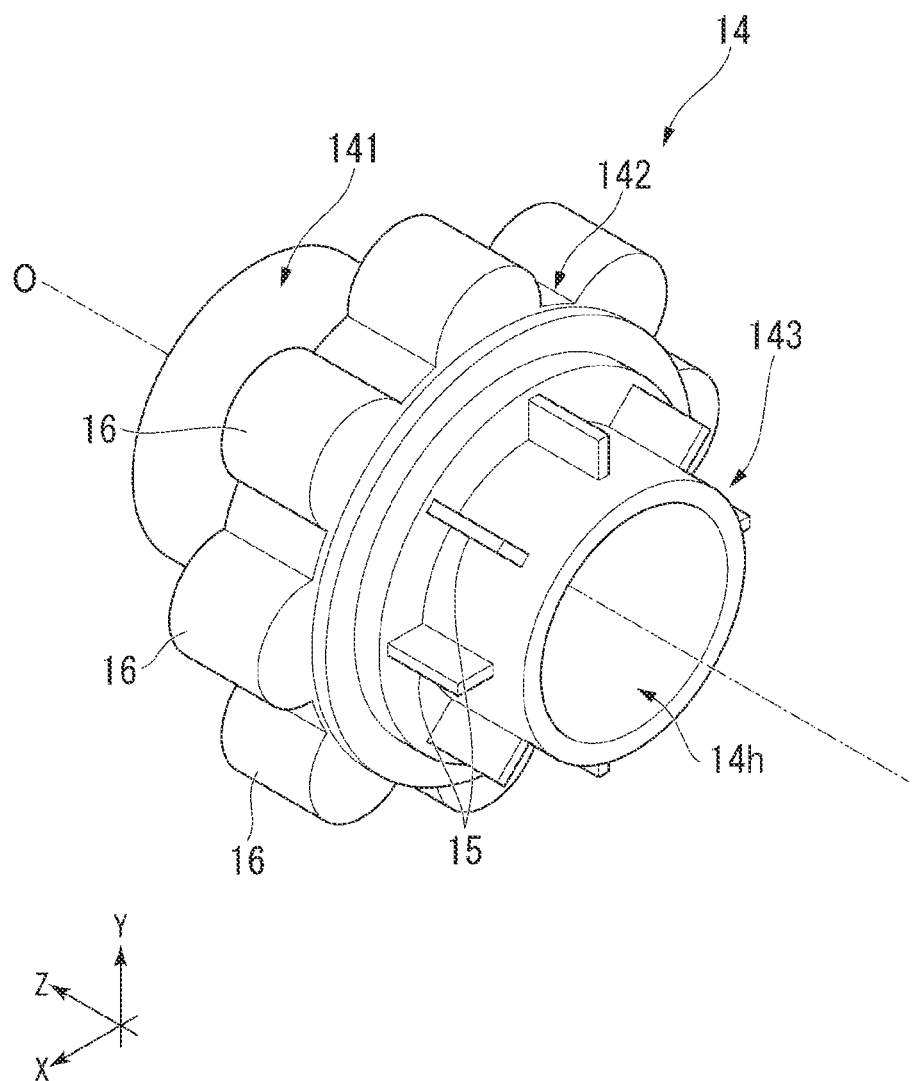
FIG. 5 is a perspective view showing an inner rotation tube of the endoscopic device from a proximal side.

FIG. 5 is a perspective view of the inner rotation tube 14 from the side of the proximal end.

The inner rotation tube 14 is a cylindrical member having a through-hole 14h through which the first rotation supporter 111 is inserted. The inner rotation tube 14 has a first inner rotation tube 141, a second inner rotation tube 142, and a third inner rotation tube 143. The first inner rotation tube 141, the second inner rotation tube 142 and the third inner rotation tube 143 are connected in this order from the distal side toward the proximal side.

The first inner rotation tube 141 is a cylindrical member with no protrusion on an outer circumferential surface. As shown in FIG. 2, an inner circumferential surface of a proximal end part of the first casing 121 is fitted with the first rotation supporter 111 with a gap to an outer circumferential surface of the first rotation supporter 111.

As shown in FIG. 5, the second inner rotation tube 142 is a cylindrical member having a larger dimension in the radial direction than that of the first inner rotation tube 141 and the third inner rotation tube 143. The second inner rotation tube 142 has the plurality of external teeth 16 arranged at equal intervals on an outer circumferential surface in the circumferential direction.

The third inner rotation tube 143 is a cylindrical member having substantially the same dimension in the radial direction as that of the first inner rotation tube 141. The third inner rotation tube 143 has a plurality of blades 15 arranged at equal intervals on an outer circumferential surface in the circumferential direction. As shown in FIGS. 4 and 5, each of the blades 15 is a flat plate-shaped part provided onto the outer circumferential surface and elongated along a normal direction of the outer circumferential surface. A plate thickness direction of the blades 15 substantially coincides with a circumferential direction of the third inner rotation tube 143.

In the embodiment, as shown in FIG. 4, the number of the external teeth 16 provided in the second inner rotation tube 142 is equal to the number of the blades 15 provided in the third inner rotation tube 143. In the cross section B-B shown in FIG. 4, the blades 15 are disposed on a line segment that connects the rotation center axis of the inner rotation tube 14 and any one of the external teeth 16.

Figure 6:
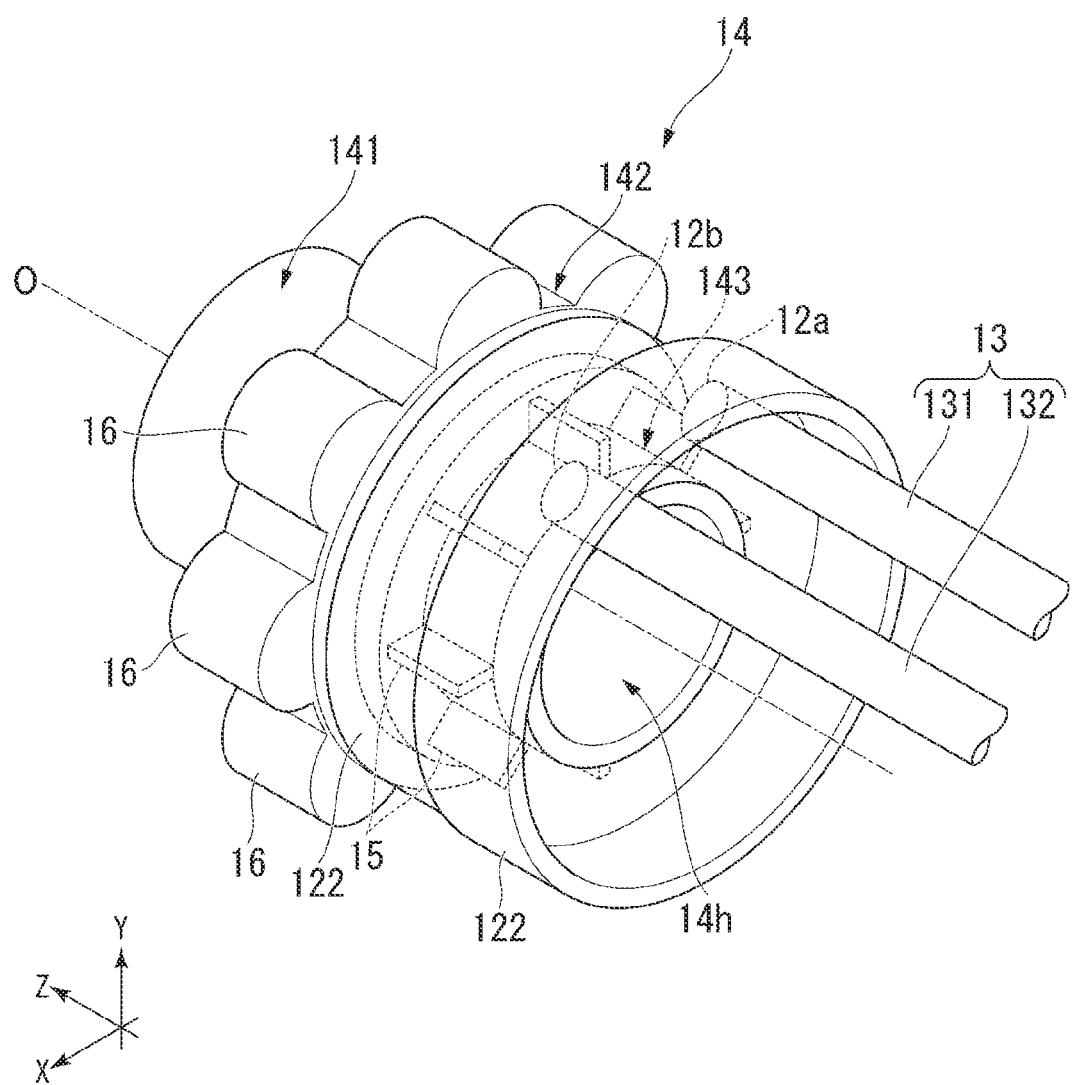
FIG. 6 is a perspective view showing a fluid duct, the inner rotation tube, and a second casing of the endoscopic device from the proximal side.

FIG. 6 is a perspective view showing the fluid duct 13, the inner rotation tube 14, and the second casing 122 from the proximal side.

As shown in FIGS. 2 and 6, the second casing 122 covers a part of the outer circumferential surface of the third inner rotation tube 143. The inner circumferential surface of the second casing 122 and the outer circumferential surface of the third inner rotation tube 143 having the blades 15 form a ring-shaped annular flow path P as shown in FIG. 4.

As shown in FIG. 6, the second casing 122 has a first supply hole 12a and a second supply hole 12b that communicate with the annular flow path P. The annular flow path P is a space with no opening except the first supply hole 12a and the second supply hole 12b.

As shown in FIG. 2, the second casing 122 includes a ring-shaped seal member 12s. Even when the inner rotation tube 14 is relatively rotated with respect to the second casing 122, the fluid passing through the annular flow path P does not leak to the outside.

As shown in FIG. 6, the fluid duct 13 has a first duct 131 and a second duct 132. Proximal ends of the first duct 131 and the second duct 132 are connected to the fluid supplier 23.

Figure 7:
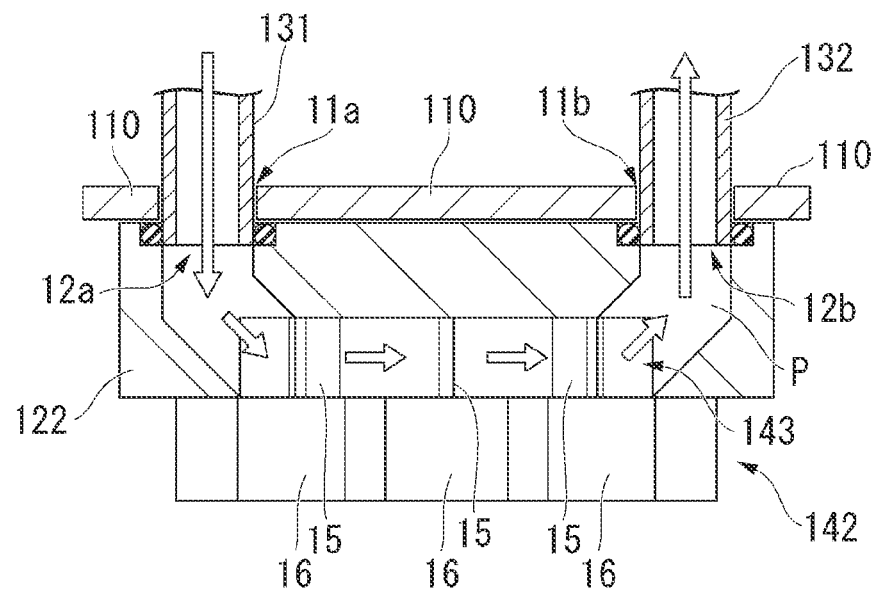
FIG. 7 is a cross-sectional view taken along a cross section C-C horizontal to a longitudinal axis of the insertion section shown in FIG. 2.
Figure 7:
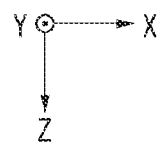
Figure 8:
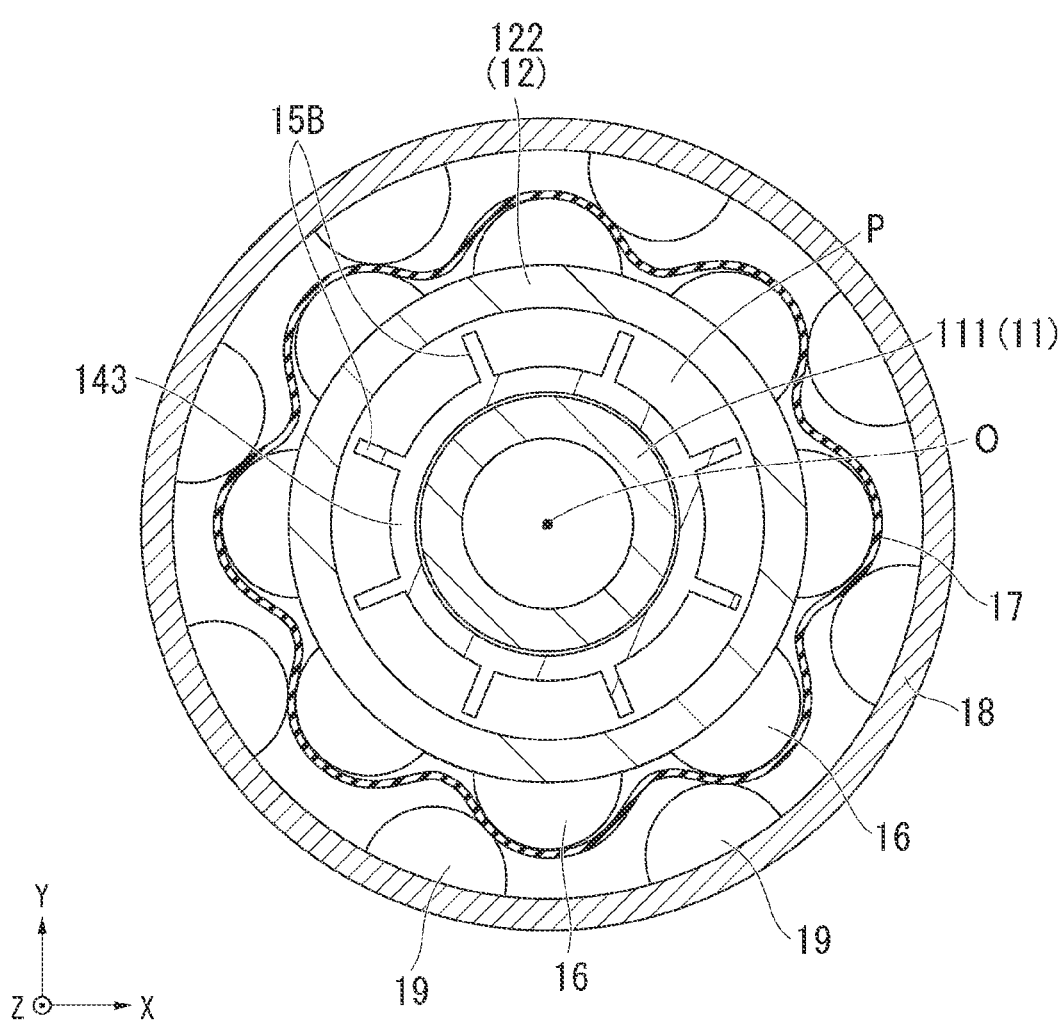
FIG. 8 is a cross-sectional view of a rotation mechanism having a modified example of a blade.

FIG. 7 is a cross-sectional view taken along a cross section C-C horizontal to the longitudinal axis O of the insertion section 2 shown in FIG. 2.

As shown in FIG. 7, the first duct 131 is connected to the annular flow path P via the first through-hole 11a formed in the connecting part 110 and the first supply hole 12a formed in the second casing 122. The fluid supplied from the first duct 131 flows into the annular flow path P via the first through-hole 11a. The fluid flowed from the annular flow path P via the first through-hole 11a is delivered to the fluid supplier 23 via the first duct 131.

As shown in FIG. 7, the second duct 132 is connected to the annular flow path P via the second through-hole 11b formed in the connecting part 110 and the second supply hole 12b formed in the second casing 122. The fluid supplied from the second duct 132 flows into the annular flow path P via the second through-hole 11b. The fluid flowing from the annular flow path P via the second through-hole 11b is delivered to the fluid supplier 23 via the second duct 132.

As shown in FIG. 3, the covering member 17 is an elastic member disposed between the inner rotation tube 14 and the outer rotation tube 18. The covering member 17 covers the inner rotation tube 14 to water-tightly seal the inside of the covering member 17. The covering member 17 is not an essential component.

As shown in FIG. 3, the outer rotation tube (the rotation member) 18 is a tubular member disposed outside the inner rotation tube 14 in the radial direction. The outer rotation tube 18 has a plurality of internal teeth 19 arranged on the inner circumferential surface in the circumferential direction. The outer rotation tube 18 is supported to be rotatable with respect to the insertion section main body 4 about the longitudinal axis O. The outer rotation tube 18 is connected to the spiral tube 9. The spiral tube 9 also rotates about the longitudinal axis O by rotating the outer rotation tube 18 about the longitudinal axis. The outer rotation tube 18 may be formed integrally with the spiral tube 9.

In the rotation mechanism 10, as shown in FIG. 2, the inner rotation tube 14 having the external teeth 16 and the outer rotation tube 18 having the internal teeth 19 function as an external gear and an internal gear inscribed thereby and which engage with each other in at least one place. The rotation mechanism 10 transmits rotational power to the outer rotation tube 18 about the longitudinal axis O of the inner rotation tube 14. As a result, the outer rotation tube 18 is rotated about the longitudinal axis O.

[Operation of Endoscopic Device 100]

Next, an operation of the endoscopic device 100 will be described.

An operator inserts the insertion section 2 with the living body insertion mechanism 6 attached to the rotation mechanism 10 into the body. The operator operates the switch 31 of the operating unit 3 and starts supply of the fluid. When the switch configured to start supply of the fluid is pushed, a signal that starts supply of the fluid is transmitted to the controller 24 via the control cable 2A. The controller 24 controls the fluid control part 24f, and starts supply of the fluid from the fluid supplier 23 to the first duct 131.

The fluid supplied from the first duct 131 flows into the annular flow path P via the first through-hole 11a. After a predetermined time elapses, the internal space of the annular flow path P is filled with the fluid, and the fluid flows out via the second through-hole 11b. The fluid flowed out of the annular flow path P via the second through-hole 11b is delivered to the fluid supplier 23 via the second duct 132.

As shown in FIG. 7, the blades 15 receive a pressure from the fluid flowing through the annular flow path P, and the inner rotation tube 14 is rotated about the longitudinal axis O. Since a plate thickness direction of the blades 15 substantially coincides with a circumferential direction of the third inner rotation tube 143, the blades 15 are easily received the pressure from the fluid flowing through the annular flow path P, and the inner rotation tube 14 is appropriately rotated around the longitudinal axis O.

The rotational power about the longitudinal axis of the inner rotation tube 14 is transmitted to the outer rotation tube 18. As a result, the outer rotation tube 18 is rotated about the longitudinal axis.

When the inner rotation tube 14 is not rotating in the direction intended by the operator, the operator may operate the switch 31 of the operating unit 3 to switch the duct through which the fluid is supplied from the first duct 131 to the second duct 132. The direction in which the inner rotation tube 14 is rotated is determined according to a status of the fluid in the annular flow path P, a position of the blade 15, or the like. The rotational direction of the inner rotation tube 14 is appropriately controlled by switching the duct through which the fluid is supplied.

The operator stops the rotational operation of the inner rotation tube 14 and the outer rotation tube 18 by operating the switch 31 of the operating unit 3 and stopping supply of the fluid.

According to the endoscopic device 100 that is the medical instrument according to the embodiment, the rotation mechanism 10 is capable of being efficiently rotated by supplying the fluid to the fluid duct 13 provided in the insertion section 2. Even when a sufficient space cannot be secured in a route through which the fluid that is a transmission member passes, the rotational power is capable of being appropriately transmitted. Even when the fluid duct 13 comes into contact with obstacles or the like in an intermediate portion, the rotational torque is capable of being transmitted to the rotation mechanism 10 as long as the fluid flows to the fluid duct 13, and the operator is capable of continuously operating the rotation mechanism 10.

According to the endoscopic device 100 that is the medical instrument according to the embodiment, since the supplied fluid is delivered to the fluid supplier 23 with no leakage in the rotation mechanism 10 to the outside, the operator is capable of performing the procedure without considering the fluid. The endoscopic device 100 uses a water that can be used in the living body as the fluid for rotating the rotation mechanism 10.

Hereinabove, while the first embodiment will be described in detail with reference to the accompanying drawings, the specific configuration is not limited to the embodiment and may include design changes or the like without departing from the spirit of the present disclosure. In addition, the components shown in the above-mentioned embodiment and another examples shown below may be appropriately combined and configured.

Modified Example 1

In the embodiment, while the blades 15 of the inner rotation tube 14 are disposed on the line segment that connects the rotation center axis of the inner rotation tube 14 and any one of the external teeth 16, the aspect of the blade of the inner rotation tube is not limited thereto. Like blades 15B that are another example of the blades 15 shown in FIG. 8, the blades may not be disposed on a line segment that connects the rotation center axis of the inner rotation tube 14 and any one of the external teeth 16. The number of the blades may not be equal to the number of the external teeth 16. The blades may be arranged at unequal intervals instead of equal intervals in the circumferential direction.

Modified Example 2

In the embodiment, while the blades 15 of the inner rotation tube 14 are flat plate-shaped members elongated from the outer circumferential surface in a normal direction of the outer circumferential surface, the aspect of the blade of the inner rotation tube is not limited thereto. The blade may have a curved surface. The blade having a curved part is largely secure a surface area in contact with the fluid, and the rotational power is capable of being more appropriately transmitted by the water pressure.

Modified Example 3

In the embodiment, while the fluid that is the transmission member is water, the aspect of the fluid is not limited thereto. The fluid that is the transmission member may be a gas such as air or the like.

Modified Example 4

In the embodiment, the rotation mechanism 10 may have a sensor configured to detect a rotation number or a rotational direction of the inner rotation tube 14. The controller 24 controls at least one of the pressure, the flow rate, and the direction of the fluid on the basis of the rotation number information obtained from the sensor. The operator is capable of controlling the inner rotation tube 14 by accurately grasping the rotation number or the rotational direction of the inner rotation tube 14.

Second Embodiment

A second embodiment will be described with reference to FIG. 9. In the following description, the components common to those already described are designated by the same reference signs, and overlapping description will be omitted. In the embodiment, the medical instrument is a surgical stapler device.

A surgical stapler device (a medical instrument) 100B according to the embodiment includes an insertion section 2 inserted into a hollow organ of a living body, an operating unit 3 provided on the proximal side of the insertion section 2, and a driving system 20.

The insertion section 2 includes an elongated insertion section main body 4 extending along a longitudinal axis O of the insertion section 2, a rotation mechanism 10B provided at a distal side of the insertion section main body 4, and a staple section 40 attached to a distal end of the rotation mechanism 10B.

Figure 9:
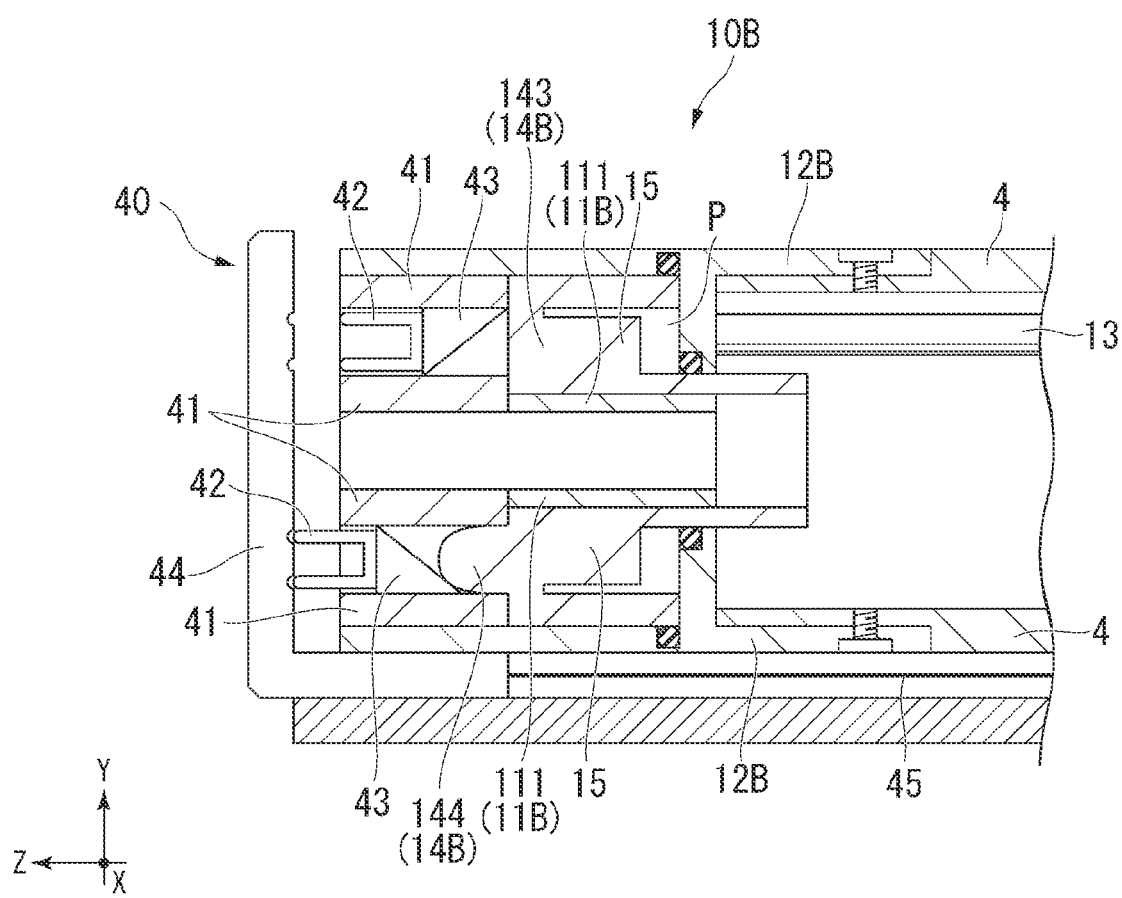
FIG. 9 is a cross-sectional view of a surgical stapler device that is a medical instrument according to a second embodiment in a longitudinal axis direction.

FIG. 9 is a cross-sectional view of the staple section 40 and the rotation mechanism 10B in a longitudinal axis direction.

As shown in FIG. 9, the rotation mechanism 10B has a rotation supporter 11B, a casing 12B, and an inner rotation tube (a power transmission member) 14B.

As shown in FIG. 9, the rotation supporter 11B has only a first rotation supporter 111 configured to rotatably support the inner rotation tube (the power transmission member) 14B. The first rotation supporter 111 is connected to a main body section 41, which will be described below.

The casing 12B is a ring-shaped member configured to cover outer circumferential parts of the inner rotation tube 14B and the staple section 40. A proximal end of the casing 12B is attached to the insertion section main body 4 on the proximal side from the inner rotation tube 14B.

The inner rotation tube (the power transmission member) 14B is a cylindrical member having a through-hole 14h through which the first rotation supporter 111 is inserted. The inner rotation tube has a convex section (a rotation member) 144 and a third inner rotation tube 143B. In the inner rotation tube 14B, the convex section (the rotation member) 144 and the third inner rotation tube 143B are arranged in this order from the distal side toward the proximal side and connected to each other.

The third inner rotation tube 143B is a ring-shaped member having a cavity therein, and the cavity opens at the proximal end. The plurality of blades 15 are arranged at equal intervals on an inner circumferential surface of the cavity in the circumferential direction.

The casing 12B covers an opening of the cavity of the third inner rotation tube 143B. The casing 12B and the cavity of the third inner rotation tube 143B form a ring-shaped annular flow path P.

The casing 12B has a first supply hole 12a and a second supply hole 12b that are in communication with the annular flow path P. The annular flow path P is a space with no opening except the first supply hole 12a and the second supply hole 12b.

The first duct 131 is connected to the annular flow path P via the first supply hole 12a formed in the casing 12B.

The second duct 132 is connected to the annular flow path P via the second supply hole 12b formed in the casing 12B.

As shown in FIG. 9, the convex section 144 is a convex-shaped member attached to the distal end of the third inner rotation tube 143B. The convex section 144 is attached to only a portion of the distal end of the third inner rotation tube 143B in the circumferential direction.

As shown in FIG. 9, the staple section 40 has a main body section 41, a staple 42, a pusher 43, an anvil 44, and a wire 45.

The main body section 41 is a ring-shaped member in which a plurality of cavities that open at the distal end thereof is formed. The plurality of cavities are arranged in the circumferential direction. The staple 42 and the pusher 43 are stored in each of the cavities so as to advance and retract.

The staple 42 is a suturing needle provided on the most distal end of the cavity of the main body section 41. The distal end of the needle is disposed toward the distal side of the staple section 40.

The pusher 43 is a member having an engaging surface that engages with the convex section 144. The pusher 43 advanced in the cavity of the main body section 41 toward a distal direction to push the staple 42 by engaging with the convex section.

The anvil 44 is a member operated by the wire 45 and configured to cause a suturing target to approach the main body section 41.

Next, an operation of a surgical stapler device 100B will be described.

The operator inserts the insertion section 2 into the body. The operator operates the wire 45 to cause the suturing target to approach the main body section 41 using the anvil 44. Next, the operator operates the switch 31 of the operating unit 3 to start supply of the fluid. When the switch configured to start supply of the fluid is pushed, a signal that starts supply of the fluid is transmitted to the controller 24 via the control cable 2A. The controller 24 controls the fluid control part 24f, and starts supply of the fluid from the fluid supplier 23 to the first duct 131.

The blades 15 receive the pressure from the fluid flowing through the annular flow path P, and the inner rotation tube 14B is rotated around the longitudinal axis. The convex section 144 is rotated in a direction around the longitudinal axis O, and the pusher 43 engaged with the convex section 144 sequentially pushes out the staples 42 to the suturing target. The suturing target is sutured by the pushed staples 42.

According to the surgical stapler device 100B that is the medical instrument according to the embodiment, like the endoscopic device 100 according to the first embodiment, the rotation mechanism 10B in capable of being efficiently rotated by supplying the fluid to the fluid duct 13 provided in the insertion section 2.

Hereinabove, while the second embodiment will be described in detail with reference to the accompanying drawings, the specific configuration is not limited to the embodiment and may include design changes or the like without departing from the spirit of the present disclosure. In addition, the components shown in the above-mentioned embodiment and the variants shown below may be appropriately combined and configured.

Modified Example 5

Figure 10:
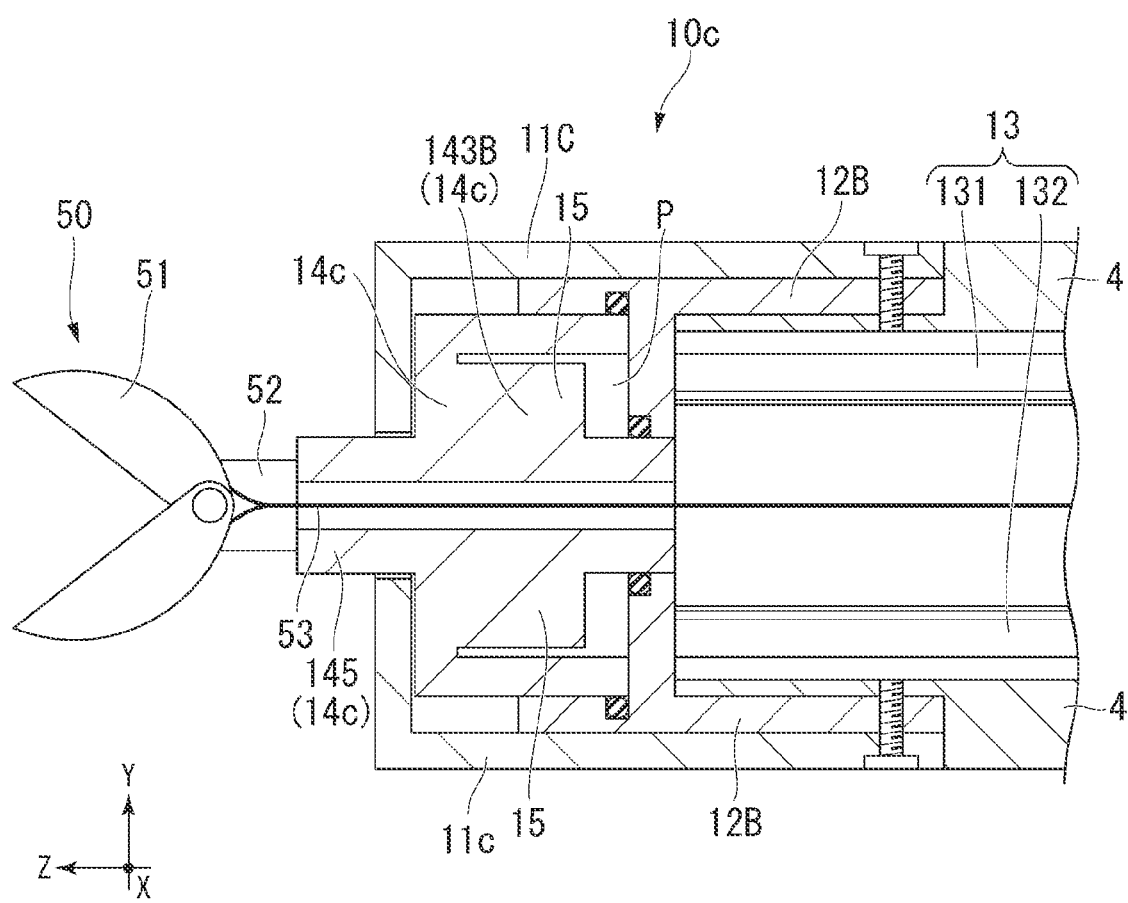
FIG. 10 is a cross-sectional view of a variant of the rotation mechanism.

In the embodiment, while the staple section 40 is attached to the distal end of the rotation mechanism 10B, the aspect of the rotation mechanism is not limited thereto. FIG. 10 is a cross-sectional view of a rotation mechanism 10C that is another example of the rotation mechanism 10B. The rotation mechanism 10C is attached to a treatment tool 50. The treatment tool 50 includes a gripping forceps 51, a support section 52 that is an action fulcrum of the gripping forceps 51, and a wire 53 configured to open and close the gripping forceps 51. The rotation mechanism 10C has an inner rotation tube 14C, and the inner rotation tube 14C includes a third inner rotation tube 143B, and a rotational power transmission section (a rotation member) 145 of a distal of the third inner rotation tube 143B. The rotational power transmission section (the rotation member) 145 is attached to the support section 52. The inner rotation tube 14C is rotated by supplying the fluid, and the gripping forceps 51 is rotated around the longitudinal axis.

As shown in FIG. 10, the rotation supporter 11C of the rotation mechanism 10C is disposed on the outer circumference side other than the inner circumference side of the inner rotation tube 14C. The rotation supporter 11C is capable of supporting the inner rotation tube 14C such that the inner rotation tube 14C rotates around the longitudinal axis even when the rotation supporter 11c is disposed on the outer circumference side of the inner rotation tube 14C.

Third Embodiment

A third embodiment will be described with reference to FIGS. 11 and 12. In the following description, the components common to those already described are designated by the same reference signs, and overlapping description will be omitted. In the embodiment, the fluid flows along the inner circumference side of the inner rotation tube other than the outer circumference.

An endoscopic device 100D that is the medical instrument according to the embodiment includes an insertion section 2 inserted into a luminal organ of a living body, an operating unit 3 provided on the proximal end of the insertion section 2, and a driving system 20.

The insertion section 2 includes an elongated insertion section main body 4 extending along the longitudinal axis O of the insertion section 2, a curved section 5 provided on the distal end part of the insertion section main body 4, a living body insertion mechanism 6, and a rotation mechanism 10D.

Figure 11:
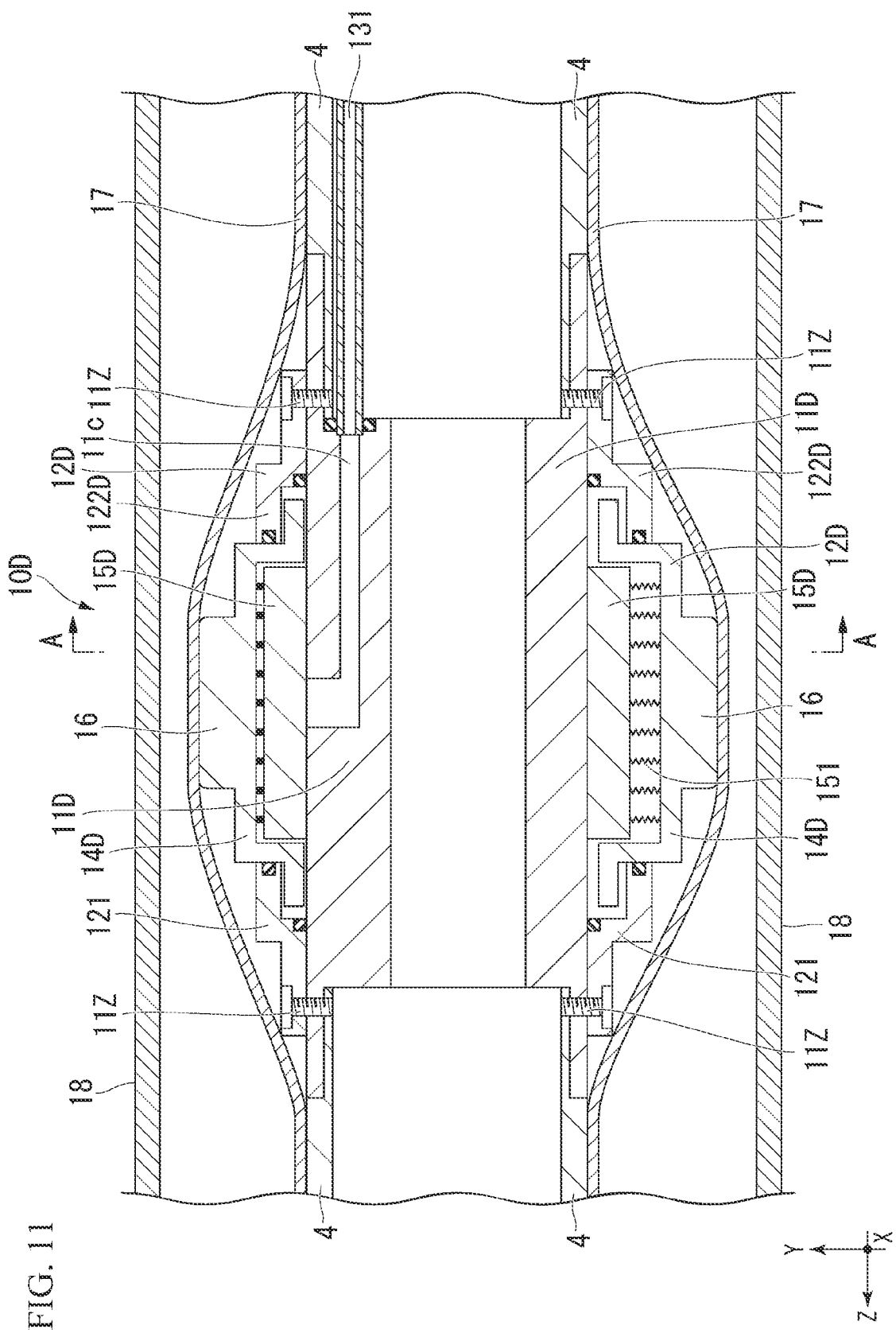
FIG. 11 is a cross-sectional view of an insertion section of the endoscopic device that is the medical instrument according to the second embodiment in the longitudinal axis direction.

FIG. 11 is a cross-sectional view of the insertion section 2 in the longitudinal axis O direction. FIG. 12 is a cross-sectional view taken along a cross section A-A perpendicular to the longitudinal axis O of the insertion section 2 shown in FIG. 11.

As shown in FIG. 11, the rotation mechanism 10D has a rotation supporter 11D, a casing 12D, an inner rotation tube (a power transmission member) 14D, a covering member 17 configured to cover the inner rotation tube 14D, and an outer rotation tube (a rotation member) 18.

The rotation supporter 11D is a cylindrical member provided in an intermediate part of the insertion section main body 4 that is flexible. The rotation supporter 11D has rigidity greater than that of the insertion section main body 4. The rotation supporter 11D rotatably supports inner rotation tube 14D fitted onto the outer circumferential part of the rotation supporter 11D. The rotation supporter 11D is connected to the insertion section main body 4 by the screws 11z at a distal part and a proximal part such that watertightness is maintained.

The rotation supporter 11D has a first through-duct 11c in communication with the first duct 131, and a second through-duct 11d in communication with the second duct 132. As shown in FIG. 12, the first through-duct 11c is connected to a first opening 11e formed in the outer circumferential surface of the rotation supporter 11D. As shown in FIG. 12, the second through-duct 11d is connected to a second opening 11f formed in the outer circumferential surface of the rotation supporter 11D.

As shown in FIG. 11, the casing 12D is a member configured to restrict advancing and retracting movement of the inner rotation tube 14 in the longitudinal direction. The casing 12D has a first casing 121 and a second casing 122D.

The second casing 122D is a ring-shaped member, and is fitted onto an outer circumference of the rotation supporter 11D. The proximal end of the second casing 122D is relatively immovably attached to the rotation supporter 11D on the proximal side from the inner rotation tube 14D. Unlike the first embodiment, in the embodiment, the annular flow path P may not be provided between the second casing 122D and the inner rotation tube 14D.

Figure 12:
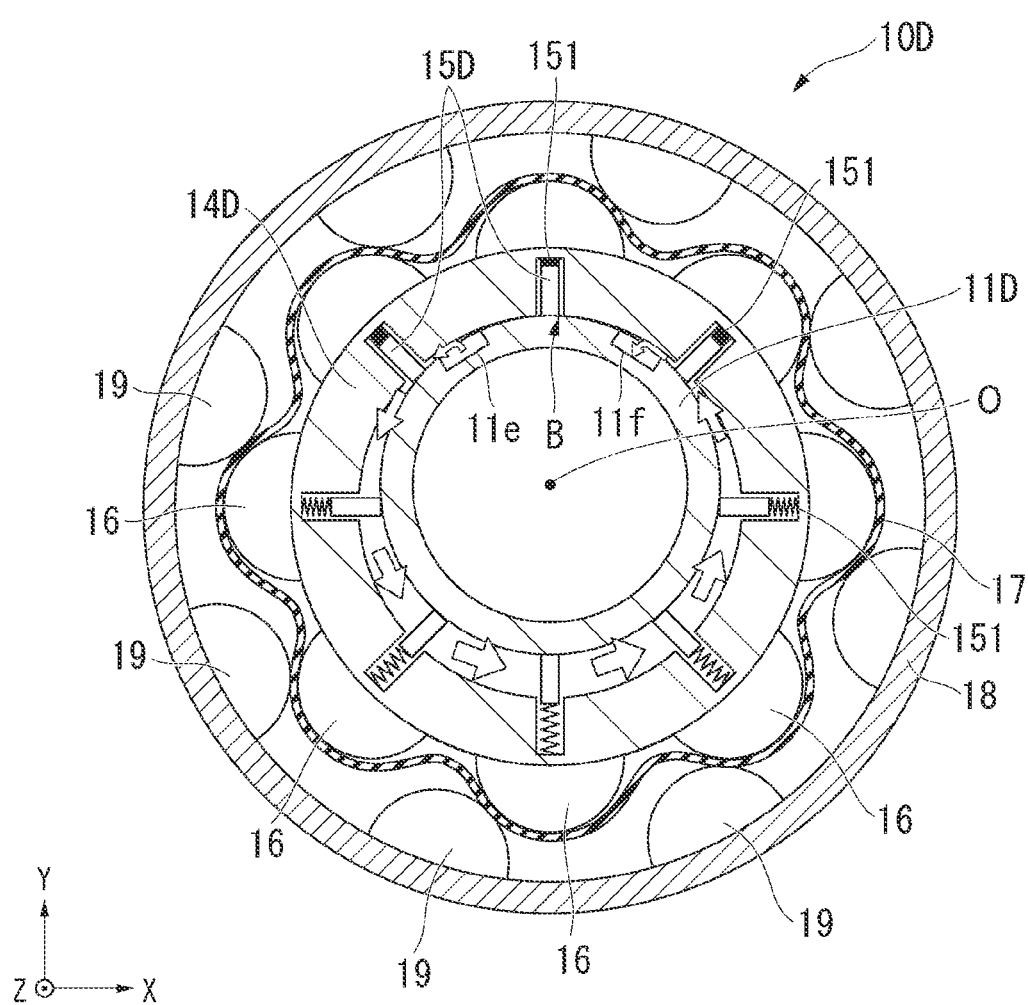
FIG. 12 is a cross-sectional view taken along a cross section A-A perpendicular to the longitudinal axis of the insertion section shown in FIG. 11.

As shown in FIG. 12, inner rotation tube (the power transmission member) 14D is a cylindrical member fitted with the first rotation supporter 11D with a gap (the annular flow path P2) with the outer circumference of the rotation supporter 11D. The inner rotation tube 14D is supported by the rotation supporter 11D so as to rotate around the longitudinal axis. The rotational center of the inner rotation tube 14D is disposed at a position eccentrically from the center of the longitudinal axis of the rotation supporter 11D. The inner rotation tube 14D comes in contact with the outer circumferential surface at only the position between the first opening 11e and the second opening 11f in the outer circumferential direction (hereinafter, referred to as "a contact section B"). As shown in FIG. 12, the inner rotation tube 14D has a plurality of external teeth 16 arranged at equal intervals on the outer circumferential surface in the circumferential direction.

The inner rotation tube 14D has the plurality of blades 15D arranged at equal intervals on the inner circumferential surface in the circumferential direction. As shown in FIG. 12, the blades 15D are accommodated in concave sections formed uniformly on the inner circumferential surface in the circumferential direction. One ends of the blades 15D are attached to the bottom sections of the concave sections via springs 151. In a state in which an external force in the normal direction of the inner circumferential surface is applied to the blades 15D, the blades 15D are supported while protruding from the concave section. When the concave section is disposed at a position coming in contact with the contact section B, all the blades 15D are accommodated in the concave sections. The blade 15D is a flat plate-shaped member. The plate thickness direction of the blade 15D substantially coincides with the circumferential direction of the inner rotation tube 14D.

The annular flow path P2 is a space with no opening except the first opening 11e and the second opening 11f.

Next, an operation of the endoscopic device 100D will be described.

The operator inserts the insertion section 2 in which the living body insertion mechanism 6 is attached to the rotation mechanism 10D into the body. The operator operates the switch 31 of the operating unit 3 and starts supply of the fluid.

The fluid supplied from the first duct 131 flows to the annular flow path P2 via the first opening 11e. After a predetermined time elapses, the internal space of the annular flow path P2 is filled with the fluid, and the fluid flows out via the second opening 11f. The fluid flowed from the annular flow path P2 via the second opening 11f is delivered to the fluid supplier 23 via the second duct 132.

As shown in FIG. 12, the fluid flowed from the first opening 11e through the annular flow path P2 flows in a direction opposite to the direction in which the contact section B is disposed (an arrow direction) and is discharged from the second opening 11f. The inner rotation tube 14D is rotated about the longitudinal axis O according to a direction in which the fluid flows. As a result, the outer rotation tube 18 is rotated about the longitudinal axis O.

Even when the inner rotation tube 14D is rotated, the position of the contact section B is not changed relatively from the rotation supporter 11D. For this reason, in the annular flow path P2, the direction in which the fluid flows is not changed.

When the rotational direction of the inner rotation tube 14D is inverted, the operator operates the switch 31 of the operating unit 3, and switches the duct into which the fluid is supplied from the first duct 131 to the second duct 132.

According to the endoscopic device 100D that is the medical instrument according to the embodiment, like the endoscopic device 100 according to the first embodiment, the rotation mechanism 10D is capable of being efficiently rotated by supplying the fluid to the fluid duct 13 provided in the insertion section. The endoscopic device 100D is capable of accurately controlling the direction of rotation. Since the endoscopic device 100D is capable of largely securing the surface area of the blades 15D in contact with the fluid in comparison with the endoscopic device 100 according to the first embodiment, the rotational power by the water pressure is capable of being more appropriately transmitted.

Hereinabove, while the third embodiment will be described in detail with reference to the accompanying drawings, the specific configuration is not limited to the embodiment and may include design changes or the like without departing from the spirit of the present disclosure. In addition, the components shown in the above-mentioned embodiment and the variants shown below may be appropriately combined and configured.

What is claimed is:

1. A medical instrument comprising:
   an insertion section main body extending along a longitudinal axis;
   a rotation supporter attached to the insertion section main body;
   a power transmission member configured to be rotatably supported by the rotation supporter, and having a blade to which a fluid is supplied;
   external teeth arranged on an outer circumferential surface of the power transmission member in a circumferential direction;
   a rotation member having a tubular shape and disposed outside the power transmission member in a radial direction;

internal teeth arranged on an inner circumferential surface of the rotation member in the circumferential direction; and a fluid duct configured to supply the fluid to the blade, wherein the power transmission member is configured to rotate by receiving power generated in the blade due to supply of the fluid, and the rotation member is configured to rotate about the longitudinal axis by receiving the power from the power transmission member as the internal teeth are meshed with the external teeth.

2. The medical instrument according to claim 1, wherein the power transmission member is a tubular member, and the power transmission member is fitted onto an outer circumferential surface of the rotation supporter.

3. The medical instrument according to claim 1, wherein the external teeth are arranged at equal intervals on the outer circumferential surface in the circumferential direction.

4. The medical instrument according to claim 1, wherein the power transmission member is a tubular member, and a plurality of the blade are arranged on the inner circumferential surface of the power transmission member in the circumferential direction.

5. The medical instrument according to claim 1, wherein the power transmission member is a tubular member, and a plurality of blade are arranged on the outer circumferential surface of the power transmission member in the circumferential direction.

6. The medical instrument according to claim 5, comprising a casing member that forms an annular flow path on the outer circumferential surface of the power transmission member so as to include the blades, wherein the fluid duct is configured to communicate with the annular flow path.

7. The medical instrument according to claim 6, further comprising a seal member having a ring-shape, and configured to prevent a fluid from flowing out from the annular flow path.

8. The medical instrument according to claim 1, further comprising:

a sensor configured to detect rotation of the rotation member; and a controller configured to control at least one of a pressure of the fluid, a flow rate and a direction of the fluid on the basis of rotation number information obtained from the sensor.

9. A medical instrument comprising:

an insertion section main body extending along a longitudinal axis;

a power transmission member having a tubular shape and supported by the insertion section main body so as to be rotatable with respect to the insertion section main body;

a rotation member disposed outside from an inner surface of the power transmission member in a radial direction; and a fluid duct configured to supply the fluid to the power transmission member, wherein the power transmission member is configured to rotate by receiving power generated due to supply of the fluid, and the rotation member is configured to rotate about the longitudinal axis in accordance with a rotation of the power transmission member.

10. The medical instrument according to claim 9, wherein the power transmission member has a blade to which a fluid is supplied, and the power transmission member is configured to rotate by receiving power generated in the blade due to supply of the fluid.

11. The medical instrument according to claim 10, wherein the blade is a flat plate-shaped member elongated from an outer circumferential surface of the power transmission member in a normal direction of the outer circumferential surface.

12. The medical instrument according to claim 10, wherein the blade has a curved surface.

13. The medical instrument according to claim 10, wherein a plurality of the blade are arranged on an inner circumferential surface of the power transmission member in a circumferential direction.

14. The medical instrument according to claim 10, wherein a plurality of blade are arranged on an outer circumferential surface of the power transmission member in a circumferential direction.

15. The medical instrument according to claim 14, comprising a casing member that forms an annular flow path on an outer circumferential surface of the power transmission member so as to include the blades, wherein the fluid duct is configured to communicate with the annular flow path.

16. The medical instrument according to claim 9, further comprising:

a sensor configured to detect rotation of the rotation member; and a controller configured to control at least one of a pressure of the fluid, a flow rate and a direction of the fluid on the basis of rotation number information obtained from the sensor.

17. The medical instrument according to claim 9, comprising a rotation supporter attached to the insertion section main body, and has a rigidity greater than a rigidity of the insertion section main body, wherein the power transmission member is rotatably fitted onto an outer circumference surface of the rotation supporter.

18. The medical instrument according to claim 9, wherein the rotation member is disposed outside the power transmission member in a radial direction.

19. The medical instrument according to claim 9, comprising:

external teeth arranged on an outer circumferential surface of the power transmission member in a circumferential direction; and internal teeth arranged on an inner circumferential surface of the rotation member in the circumferential direction, wherein the rotation member is configured to rotate about the longitudinal axis by receiving the power from the power transmission member as the internal teeth are meshed with the external teeth.

20. The medical instrument according to claim 19, wherein the external teeth is arranged at equal intervals on the outer circumferential surface in the circumferential direction.

* * * * *